(12) United States Patent
Castañeda et al.

(10) Patent No.: US 7,001,401 B1
(45) Date of Patent: Feb. 21, 2006

(54) DEVICE AND METHOD FOR HOLDING A BLOOD VESSEL

(75) Inventors: Javier E. Castañeda, Miami, FL (US); Ralph de la Torre, Swampscott, MA (US)

(73) Assignee: Medcanica LLC, Miami, FL (US)

( * ) Notice: Subject to any disclaimer, the term of this patent is extended or adjusted under 35 U.S.C. 154(b) by 195 days.

(21) Appl. No.: 10/430,118

(22) Filed: May 6, 2003

(51) Int. Cl.
*A61B 17/04* (2006.01)

(52) U.S. Cl. .................. 606/148; 606/144; 606/150

(58) Field of Classification Search ............... 606/139, 606/144, 148, 150, 167, 185; 604/162, 198
See application file for complete search history.

(56) References Cited

U.S. PATENT DOCUMENTS

| | | | |
|---|---|---|---|
| 4,854,318 A | | 8/1989 | Solem et al. |
| 4,911,164 A | * | 3/1990 | Roth ........................... 606/148 |
| 5,053,043 A | * | 10/1991 | Gottesman et al. ......... 606/148 |
| 5,439,467 A | * | 8/1995 | Benderev et al. ........... 606/139 |
| 5,480,407 A | * | 1/1996 | Wan et al. .................. 606/148 |
| 5,752,964 A | * | 5/1998 | Mericle ....................... 606/148 |
| 5,792,152 A | * | 8/1998 | Klein et al. ................. 606/144 |
| 6,123,084 A | * | 9/2000 | Jandak et al. ............... 128/898 |
| 6,206,893 B1 | * | 3/2001 | Klein et al. ................. 606/144 |
| 6,355,050 B1 | | 3/2002 | Andreas et al. |
| 6,494,893 B1 | * | 12/2002 | Dubrul et al. .............. 606/185 |
| 6,517,553 B1 | * | 2/2003 | Klein et al. ................. 606/144 |

* cited by examiner

*Primary Examiner*—Glenn K. Dawson
*Assistant Examiner*—Michael Mendoza
(74) *Attorney, Agent, or Firm*—Gordon & Jacobson, P.C.

(57) ABSTRACT

A device for holding a blood vessel (and corresponding method of operation) includes a mandrel having a proximal end opposite a distal end. A tube houses a portion of the mandrel. A tip assembly, which is operably coupled to the distal end of the mandrel, comprises a sheath having a tapered portion and a cylindrical portion. The sheath is adapted to be inserted into a lumen of a blood vessel such that an end of the blood vessel is supported by the tapered portion. The elastic nature of the blood vessel holds the end of the blood vessel in place with respect to the tip assembly. The tapered portion includes an exterior surface with a plurality of needle-guide-grooves that extend along such exterior surface. A needle is driven through the blood vessel while being guided by a needle-guide groove such that the needle is driven through the blood vessel near the end of the blood vessel.

34 Claims, 5 Drawing Sheets

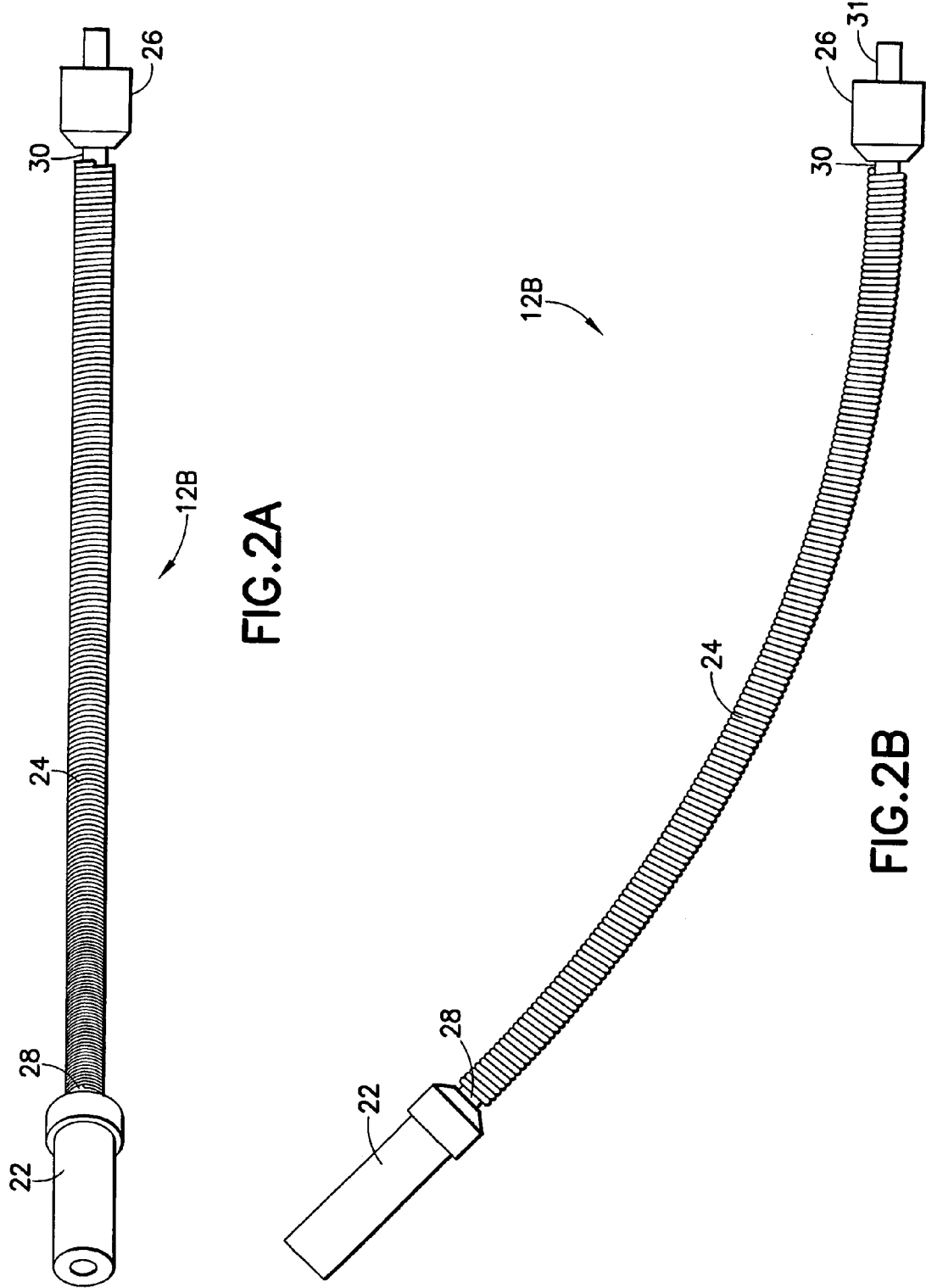

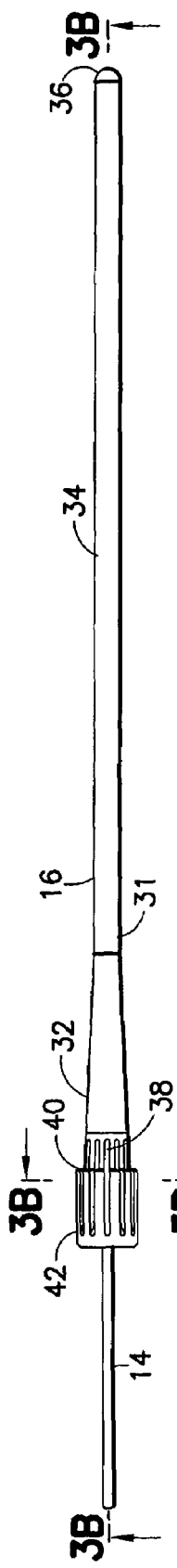
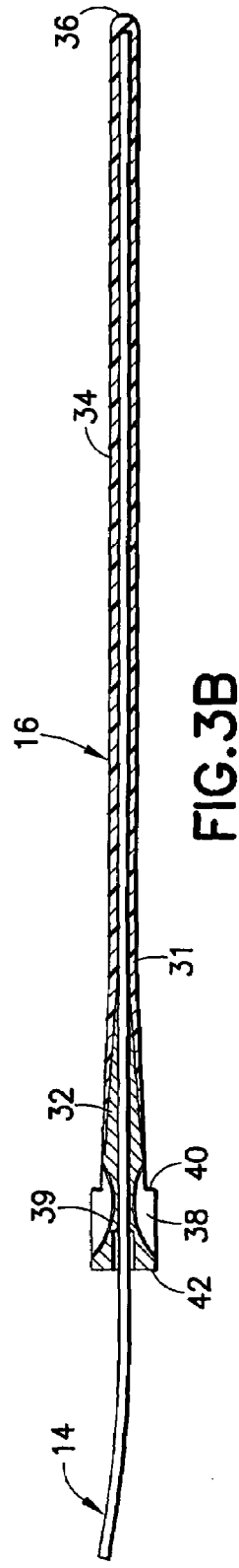
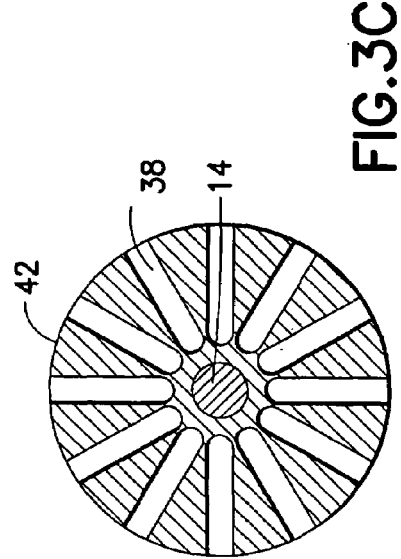

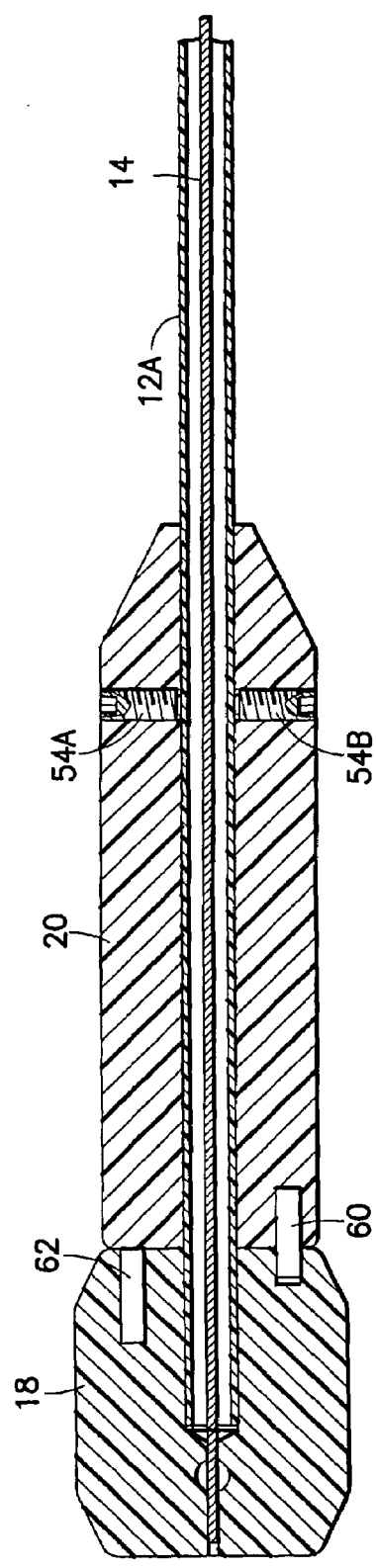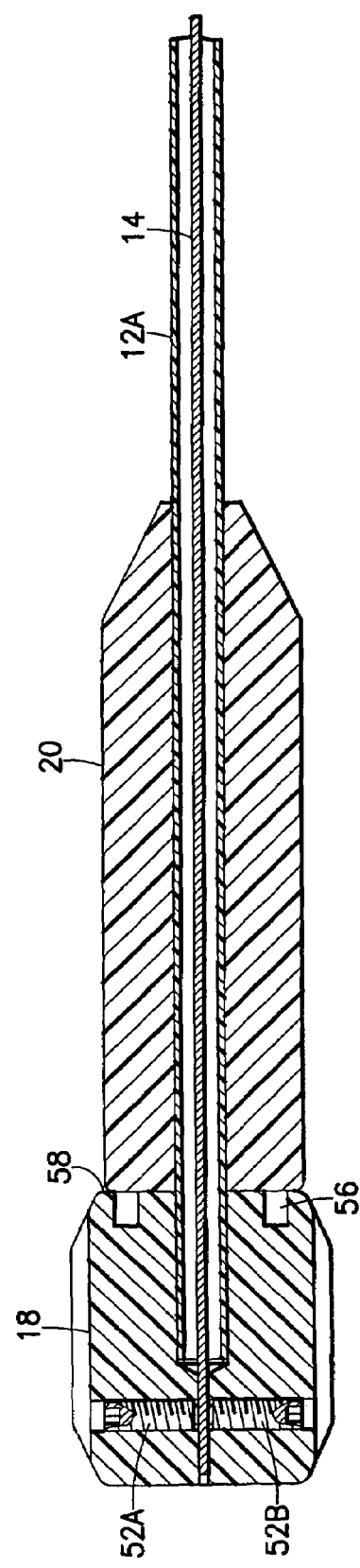

DEVICE AND METHOD FOR HOLDING A BLOOD VESSEL

BACKGROUND OF THE INVENTION

1. Field of the Invention

This invention relates to surgical devices and methods. More particularly, this invention relates to devices and methods for holding a blood vessel. While not limited thereto, the invention has particular application to the suturing of a blood vessel during endoscopic surgery.

2. State of the Art

When suturing a blood vessel, such as when performing an anastomosis (connection between two blood vessels), it is necessary to hold the end of the blood vessel such that the suture needle can be inserted at the proper location.

In a typical coronary artery bypass (CABG) surgical procedure, a blood vessel is grafted from another part of the body and it is connected to the blocked coronary artery past the blockage. In this case, one end of the grafted vessel is attached with sutures to the side of the coronary artery. In open-chest CABG procedures this is accomplished by having an assistant hold the open end of the grafted vessel with tweezers while the operator (surgeon) passes the needle through the edge of the vessel.

A typical anastomosis requires about twelve sutures equally spaced apart to make a secure connection. When performing this procedure endoscopically or with very small incisions (to minimize trauma to the patient), it is very difficult to hold the grafted vessel with tweezers for suturing because of space limitations. The difficulties are accentuated by the natural properties of the grafted vessels. The grafted vessel is very supple, slippery and irregular on the outside. It stretches considerably, moving out of the way when the operator tries to push the needle through it. Additionally, the operator must be careful not to damage or disrupt the inside of the grafted vessel wall (intima) as this can lead to circulation problems, including complete blockage.

The grafted vessel is usually either a vein taken out of the leg, or an artery taken from inside the chest wall. The arteries used from the chest wall are the internal mammary arteries (IMA). Most commonly the Left Internal mammary (LIMA) is used since most bypasses are done on the left side of the heart. Using an internal mammary artery has the advantage of only requiring one anastomosis: from the transected end of the graft to the side of the coronary artery. The other end of the internal mammery artery remains connected at its native juncture.

Thus, there remains a need in the art for an improved device (and corresponding method of operation) that holds a vessel in a fixed position and is suitable for use in space-constrained environments such as during suturing of a vessel graft in an endoscopic procedure.

SUMMARY OF THE INVENTION

It is therefore an object of the invention to provide a device (and corresponding method of operation) that holds a blood vessel in a fixed position, which is suitable for use in space-constrained environments, such as during suturing of a vessel graft in an endoscopic procedure.

It is another object of the invention to provide a device (and corresponding method of operation) that holds a blood vessel taut to facilitate piercing without damage to the intima of the vessel.

It is a further object of the invention to provide a device (and corresponding method of operation) that holds a blood vessel from the inside, freeing up the space around it for access to the blood vessel or for other functions.

It is an additional object of the invention to provide a device (and corresponding method of operation) that holds a blood vessel and allows for controlled rotation of the blood vessel for optimal needle access around the vessel circumference.

It is a further object of the invention to provide a device (and corresponding method of operation) that holds a blood vessel and allows for controlled rotation of the blood vessel with built-in limits to avoid twisting of the blood vessel.

It is also an object of the invention to provide a device (and corresponding method of operation) that holds a blood vessel and facilitates equal spacing between sutures.

It is also an object of the invention to provide a device (and corresponding method of operation) that holds a blood vessel and affords flexibility such that the device can bend to avoid a body part/object or to improve the field of view of the operator/assistants.

It is still another object of the invention to provide a device (and corresponding method of operation) that is suitable for holding a variety of blood vessels of different sizes.

In accord with these objects, which will be discussed in detail below, a device for holding a blood vessel (and corresponding method of operation) includes a mandrel having a proximal end opposite a distal end. A tube houses a portion of the mandrel. A tip assembly, which is operably coupled to the distal end of the mandrel, comprises a sheath having a tapered portion and a cylindrical portion. The sheath is adapted to be inserted into a lumen of a blood vessel such that an end of the blood vessel is supported by the tapered portion. The elastic nature of the blood vessel holds the end of the blood vessel in place with respect to the tip assembly. The tapered portion includes a plurality of needle-guide-grooves that extend along the exterior surface of the tapered portion. A needle is driven through the blood vessel while being guided by a needle-guide groove such that the needle is driven through the blood vessel near the end of the blood vessel.

It will be appreciated that the device holds a blood vessel taut, which facilitates piercing without damage to the intima of the vessel. Moreover, by holding the blood vessel from the inside, space is freed up around it for access to the blood vessel or for other functions. In addition, the tapered outer diameter of the tapered portion (which may be customized for different vessel sizes) enables the device to hold a variety of blood vessels of different sizes.

According to one embodiment, the tube and the tip assembly are adapted to be inserted through an endoscopic port, which makes the device suitable for use in endoscopic surgical operations.

According to another embodiment of the invention, rotation of the tapered portion of the tip assembly is controlled by a user rotating a knob affixed to the mandrel. Such controlled rotation is used to drive one or more needles through the vessel circumference while being accurately guided by different needle-guide grooves. In addition, such rotation may be controlled with built-in limits (preferably realized by a pair of pins) to avoid twisting of the blood vessel.

According to yet another embodiment of the present invention, the needle-guide-grooves are evenly spaced about the circumference of the tapered portion, which facilitates equal spacing between needle punctures and the corresponding fasteners.

According to still yet another embodiment of the present invention, the tube includes a malleable section, which affords flexibility such that the device can bend to avoid a body part/object or to improve the field of view of the operator/assistants.

Additional objects and advantages of the invention will become apparent to those skilled in the art upon reference to the detailed description taken in conjunction with the provided figures.

BRIEF DESCRIPTION OF THE DRAWINGS

FIGS. 2A and 2B are magnified perspective views of the tube section 12B of FIG. 1 in accordance with the present invention;

FIG. 3A is a magnified side elevational view of the tip assembly of FIG. 1 in accordance with the present invention;

FIG. 3B is a cross-sectional view through line A—A of FIG. 3A;

FIG. 3C is a cross-sectional view through line B—B of FIG. 3A;

FIGS. 5A and 5B are magnified cross-sectional views of the knob and handle of the device of FIG. 1 in accordance with the present invention.

DETAILED DESCRIPTION OF THE PREFERRED EMBODIMENTS

As used herein, the term "distal" is generally defined as in the direction of the patient, or away from a user of the device. Conversely, "proximal" generally means in the direction away from the patient, or toward the user of the device. The term "suture" and "suturing" are herein intended to include the process of joining tissue together with a fastener to close an aperture, opening, or wound. The fastener is usually a thread of material (either polymeric or natural), gut, wire or the like. The fastener may also be a clamp, stud, hasp, hook, staple or other tissue coupling member.

Figure 1:
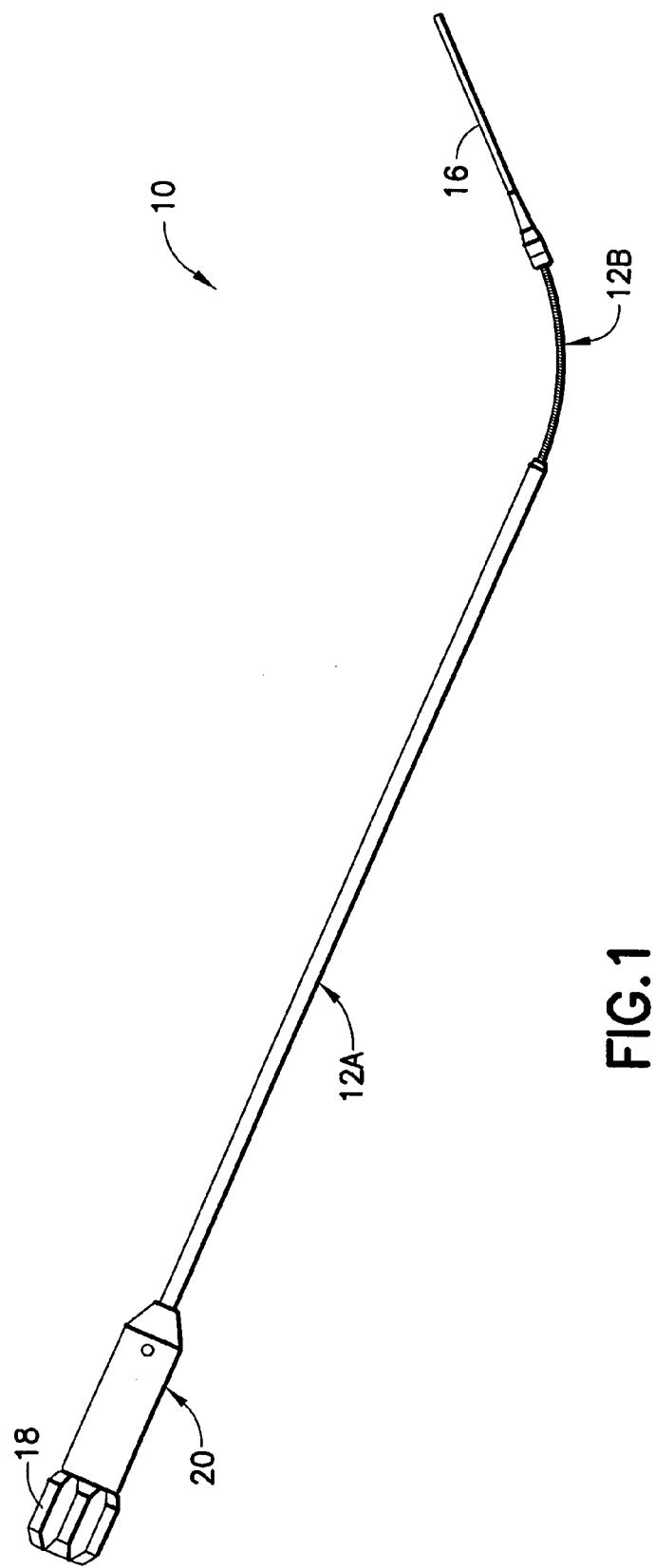
FIG. 1 is a perspective view of a blood vessel holding device in accordance with the present invention.

Turning now to FIG. 1, a blood vessel holder 10 in accordance with the present invention includes a tube 12 (shown as two parts 12A and 12B) that houses a flexible core wire 14 (shown in FIGS. 3A–3C), which is referred to herein as a 'mandrel'. Preferably, the diameter of the mandrel is on the order of 0.025 inches (0.64 mm). A tip assembly 16 is affixed to the distal end of the mandrel 14. Preferably, the diameters of the tube 12 and tip assembly 16 are small (e.g., typically less than 10 millimeters) such that they readily fit through an endoscopic port for use in minimally invasive surgery. A knob 18 is affixed to the proximal end of the mandrel 14. When the knob 18 is rotated, the mandrel 14 rotates along with the tip assembly 16 affixed to the mandrel 14. A handle 20 is affixed to the proximal end of the tube 12. Both the handle 20 and tube 12 are free to rotate about the mandrel 14 housed therein.

The tube 12 preferably includes a rigid (or semi-rigid) section 12A at its proximal end and a malleable section 12B at its distal end. As shown in FIGS. 2A and 2B, the malleable section 12B preferably includes an adapter 22, a coil 24 and a collar 26. The adapter 22 mates to the distal end of the rigid section 12A. The collar 26 mates to the tip assembly 16. The coil 24 extends between a tubular section 28 of the adapter 22 and tubular section 30 of the collar 26. The mandrel 14 is housed within a passageway through the adapter 22, coil 24 and collar 26. The bend radius of the coil 24 (and mandrel 14 housed therein) is flexible, which enables the tubular section 12B to bend without kinking as shown in FIG. 1 and FIG. 2B.

As shown in FIGS. 3A–3C, the tip assembly 16 is affixed (preferably by molding) to the distal portion of the mandrel 14 (which extends beyond the distal end of the tube 12). The tip assembly 16 includes a sheath 31 having a tapered portion 32 and a cylindrical portion 34, which is disposed at the distal end of the tip assembly 16. The length of the sheath 31 is preferably on the order of 0.8 inches (20 mm). The diameter of the cylindrical portion 34 is preferably about 0.05 inches (1.25 mm) such that it can be inserted into the lumen of the blood vessel that is to be held. In addition, the cylindrical portion 34 is preferably made of polymeric material such as nylon or polyurethane so that the distal end of the tip assembly 16 remains flexible and atruamatic to the interior of the vessel to be held. In addition, the cylindrical portion 34 preferably has a rounded tip 36 to facilitate insertion into the lumen of the vessel to be held.

The tapered portion 32 of the sheath has a circular (or substantially-circular) cross section with an outer diameter (OD) that tapers from a larger OD value, such as 0.17 inches (4.3 mm), at or near its proximal end to a smaller OD value, such as 0.05 inches (1.25 mm) at or near its distal end. The exterior surface of a portion (referred to below as "grooved portion") of the tapered portion 32 includes a plurality of has needle-guide-grooves 38, which preferably extend in a direction substantially parallel to the longitudinal axis of the tapered portion 32 as best shown in FIG. 3A.

The sheath 31 is inserted into the blood vessel such that the proximal end of the vessel is stretched/deformed by the grooved portion of the tapered portion 32 and the elastic nature of the blood vessel holds the blood vessel in its place over the sheath 31. The depth of the needle-guide-grooves 38 properly guide a needle such that it is driven through the blood vessel near the edge of the held blood vessel. A fastener, which is coupled to the needle, is used to suture the blood vessel to its target site. Alternatively, the needle may be an integral part of the fastener. In a coronary artery bypass (CABG) surgical procedure, the target site is a portion of a blocked coronary artery past the blockage.

Preferably, the proximal end of the tapered portion 32 terminates at a ledge 40 that extends radially outward to an end section 42. The end section 42 preferably has a constant (or substantially-constant) outer diameter as best shown in the cross-section of FIG. 3C. The exterior surface of the end section 42 includes the needle-guide-grooves 38, which extend through the ledge 40 to the tapered portion 32 in a direction substantially parallel to the longitudinal axis of the end section 42 and tapered portion 32 as best shown in FIG. 3A.

Figure 4B:
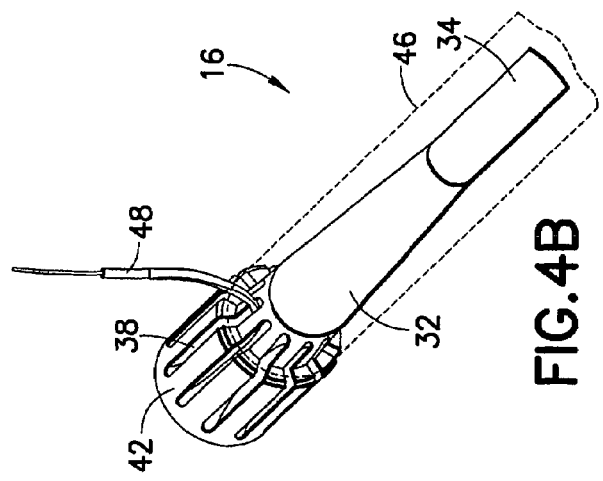
FIG. 4B is a magnified perspective view of the tip assembly of FIG. 3A shown holding a blood vessel in accordance with the present invention.
Figure 4A:
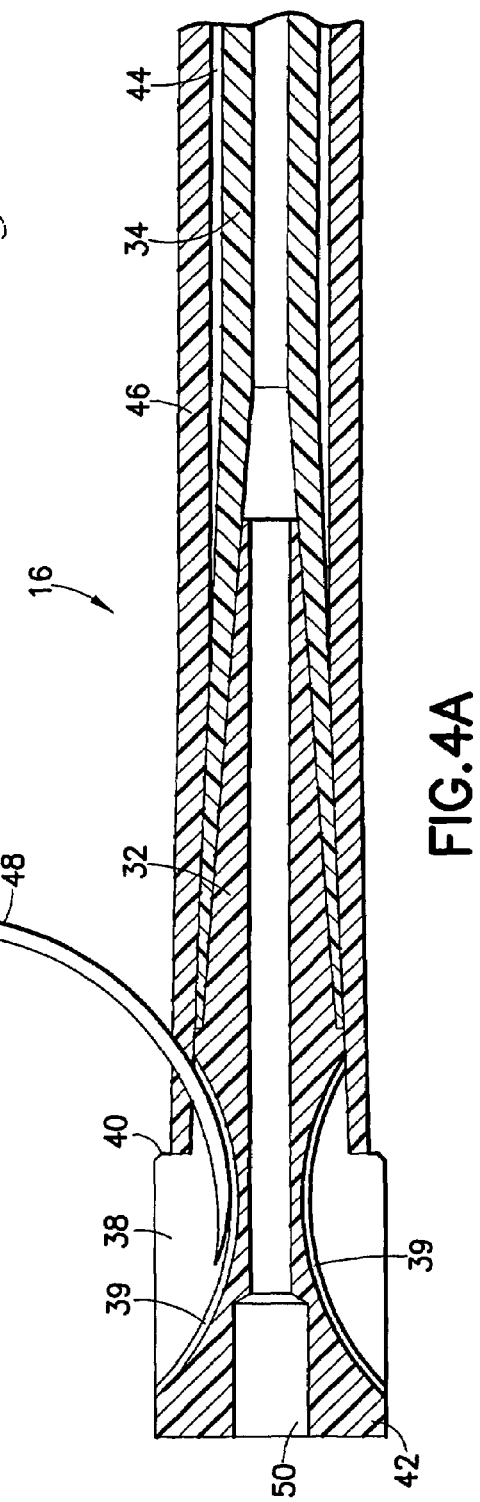
FIG. 4A is a magnified cross-sectional view of the tip assembly of FIG. 3A shown holding a blood vessel in accordance with the present invention.

As shown in FIGS. 4A and 4B, during operation, the sheath 31 (including the tapered portion 32) is inserted into a lumen 44 of a blood vessel 46 until the proximal end of the vessel 46 butts up against the ledge 40. The large outer diameter of the tapered portion 32 near the ledge 40 stretches and deforms the blood vessel 40, and the elastic nature of the blood vessel 40 holds the proximal end of the blood vessel 40 in place butting up against the ledge 40. As best shown in FIGS. 3B, 3C and 4A, the depth profile of the needle-guide-grooves 38 properly guide a needle such that it is driven through the blood vessel 40 near the edge of the held blood vessel 40. Thus, the grooves 38 preferably include a smooth curved surface 39 whose contour matches the curvature of the needle 48. Preferably, the grooves 38 are spaced apart every fifteen degrees about the outer circumference of the end section 42 and tapered portion 32 as best shown in FIG. 3C.

The proximal end of the tip assembly 16 preferably includes a bore 50 (as best shown in FIG. 4A) that accepts a mating tube section 31 of the collar 26 as shown in FIGS. 2A and 2B. The mating tube section 31 acts as an axle over which the tip assembly 16 can rotate.

As shown in FIGS. 5A and 5B, set screws 52A and 52B are preferably used to affix the knob 18 to the proximal end of the mandrel 14, and set screws 54A and 54B are preferably used to affix the handle 20 to the proximal end of the tube section 12A. Alternatively, adhesive bonds may be used to affix the knob 18 to the proximal end of the mandrel 14 and to affix the handle 20 to the proximal end of the tube section 12A.

As described above, the knob 18 may be rotated with respect to the handle 20 to rotate the mandrel 14 and the tip assembly 16 affixed thereto. In this configuration, during operation, the user can easily control rotation of the knob 18 and corresponding rotation of the blood vessel held by the tip assembly 16 such that one or more needles are driven through the blood vessel around the circumference of the held blood vessel near its proximal end. One or more fasteners, which are coupled to the one or more needles, are used to suture the blood vessel to its target site. Alternatively, the needle(s) may be an integral part of the fastener(s).

Preferably, the rotation of the knob 18 (and corresponding rotation of the tip assembly 16 and held blood vessel) is limited by a circumferential groove 56 disposed on the side 58 of the knob 18 facing the handle 20 as shown. A pin 60 in the handle 20 races in the groove 56 until it hits another pin 62, which is affixed to the knob 18. In this configuration, the pins 60, 62 cooperate to limit the rotation of the knob 18 to just under one turn.

There have been described and illustrated herein an embodiment of a device for holding a blood vessel and a corresponding method of operation. While particular embodiments of the invention have been described, it is not intended that the invention be limited thereto, as it is intended that the invention be as broad in scope as the art will allow and that the specification be read likewise. Thus, while the description above describes a knob that provides manual rotation control of the tip assembly of the device, it will be appreciated that other rotation control mechanisms (such as automatic motor-based rotation control mechanisms) may be used to provide rotation control of the tip assembly of the device as well. In addition, while particular geometries and dimensions of the tip assembly elements (e.g., sheath, tapered portion, needle-guide groove profiles, end section) have been disclosed, it will be understood that other geometries and dimensions can be used. Also, while it is preferred that the rotation-limiting stop pin assembly be integrated into the handle and knob of the device, it will be recognized that such features can be integrated to other parts of the device. Moreover, while particular configurations have been disclosed, it will be appreciated that other configurations could be used as well. For example, the outer tube can be designed to be remotely steerable. In addition, the device can be oriented relative to a surgical site by a variety of means, such as by being attached to a port or bracket (typically rib mounted); being attached to a bed frame via a bracket; locking the distal end to an instrument inside the body, such as a heart stabilizer; or by suturing the distal end to the area surrounding the site of anastomosis. It will therefore be appreciated by those skilled in the art that yet other modifications could be made to the provided invention without deviating from its spirit and scope as claimed.

What is claimed is:

1. A device for holding a blood vessel having a lumen comprising:
   a mandrel having a proximal end and a distal end;
   a tube that houses a portion of said mandrel between said proximal end and said distal end of said mandrel; and
   a tip assembly, operably coupled to said distal end of said mandrel, comprising a sheath having a tapered portion and a cylindrical portion, said cylindrical portion having a vessel-receiving tip, said sheath adapted to be inserted into the lumen of the blood vessel such that an end of the blood vessel is supported by said tapered portion, said tapered portion having a tapered exterior surface that is spaced apart from said vessel-receiving tip and a plurality of needle-guide-grooves that extend in a longitudinal direction along said tapered exterior surface.

2. A device for holding a blood vessel according to claim 1, further comprising:
   rotation means for rotating said tapered portion of said tip assembly.

3. A device for holding a blood vessel according to claim 2, wherein:
   said tapered portion is affixed to said mandrel, and said rotation means comprises a knob affixed to said proximal end of said mandrel.

4. A device for holding a blood vessel according to claim 1, wherein:
   said mandrel is rotatable with respect to said tube.

5. A device for holding a blood vessel according to claim 4, further comprising:
   a handle affixed to a proximal end of said tube, wherein said mandrel is rotatable with respect to said handle.

6. A device for holding a blood vessel according to claim 1, wherein:
   said tube and tip assembly are adapted to be inserted through an endoscopic port.

7. A device for holding a blood vessel according to claim 1, wherein:
   said cylindrical portion is made of a polymeric material.

8. A device for holding a blood vessel according to claim 1, wherein:
   said vessel-receiving tip comprises a rounded tip.

9. A device for holding a blood vessel according to claim 1, wherein:
   said tube includes a rigid section at its proximal end and a malleable section at its distal end.

10. A device for holding a blood vessel according to claim 9, wherein:
   said malleable section includes an adapter, a flexible coil, and a collar, said adapter mating to a distal end of said rigid section, said collar mating to said tip assembly, and said coil disposed between said adapter and said collar.

11. A device for holding a blood vessel according to claim 10, wherein:
   said tip assembly includes a proximal end having a bore, and said collar includes a mating tube adapted to fit in said bore.

12. A device for holding a blood vessel according to claim 1, wherein:
said tapered portion is rotatable relative to said tube.

13. A device for holding a blood vessel according to claim 1, wherein:
said plurality of needle-guide-grooves are evenly spaced apart about an outer circumference of said tapered portion.

14. A device for holding a blood vessel according to claim 13, wherein:
said plurality of needle-guide-grooves have a longitudinal curved shape to accommodate a curved needle.

15. A device for holding a blood vessel according to claim 1, wherein:
said tip assembly includes a ledge that is used as a stop to locate the end of the blood vessel.

16. A device for holding a blood vessel according to claim 1, further comprising:
a knob fixed to said mandrel, and a handle fixed to said tube, wherein said handle is rotatable with respect to said knob.

17. A device for holding a blood vessel according to claim 16, further comprising:
a stop that limits rotation of said knob and handle relative to one another.

18. A device for holding a blood vessel according to claim 17, wherein:
said stop comprises a pair of pins that cooperate to limit rotation of said knob relative to said handle.

19. A method of holding a blood vessel having a lumen comprising the steps of:
i) providing a device including
a mandrel having a proximal end and a distal end,
a tube that houses a portion of said mandrel between said proximal end and said distal end of said mandrel, and
a tip assembly that is operably coupled to said distal end of said mandrel and that comprises a sheath having a tapered portion and a cylindrical portion, said tapered portion having an exterior surface including a plurality of needle-guide-grooves that extend along said exterior surface;
ii) inserting said sheath into the lumen of the blood vessel such that an end of the blood vessel is supported by said tapered portion; and
iii) driving a needle through the vessel while being guided by at least one of said plurality of needle-guide grooves such that said needle is driven through the blood vessel near the end of the blood vessel.

20. A method of holding a blood vessel according to claim 19, further comprising the steps of:
repeatedly rotating said tapered portion of said tip assembly and driving said needle or at least one other needle around the circumference of the end of the blood vessel while being guided by different needle-guide grooves.

21. A method of holding a blood vessel according to claim 20, wherein:
said device further includes a knob affixed to said proximal end of said mandrel.

22. A method of holding a blood vessel according to claim 21, wherein:
said rotating the tapered portion is accomplished by rotating said knob.

23. A method of holding a blood vessel according to claim 19, wherein:
said mandrel is rotatable with respect to said tube.

24. A method of holding a blood vessel according to claim 23, wherein:
said device further comprises a handle affixed to a proximal end of said tube.

25. A method of holding a blood vessel according to claim 19, further comprising the step of:
inserting said tube and tip assembly through an endoscopic port into a human body.

26. A method of holding a blood vessel according to claim 19, wherein:
said cylindrical portion is made of a polymeric material.

27. A method of holding a blood vessel according to claim 19, wherein:
said cylindrical portion has a rounded tip.

28. A method of holding a blood vessel according to claim 19, wherein:
said tube includes a rigid section at its proximal end and a malleable section at its distal end.

29. A method of holding a blood vessel according to claim 28, wherein:
said malleable section includes an adapter, a flexible coil, and a collar, said adapter mating to a distal end of said rigid section, said collar mating to said tip assembly, and said coil disposed between said adapter and said collar.

30. A method of holding a blood vessel according to claim 29, wherein:
said tip assembly includes a proximal end having a bore, and said collar includes a mating tube adapted to fit in said bore.

31. A method of holding a blood vessel according to claim 19, wherein:
said tapered section is rotatable relative to said tube.

32. A method of holding a blood vessel according to claim 19, wherein:
said plurality of needle-guide-grooves are evenly spaced apart about an outer circumference of said tapered portion.

33. A method of holding a blood vessel according to claim 32, wherein:
said plurality of needle-guide-grooves have a longitudinal curved shape to accommodate a curved needle.

34. A method of holding a blood vessel according to claim 19, wherein:
said tip assembly includes a ledge, and
said inserting comprising inserting said sheath into the lumen of the blood vessel until the end of the blood vessel is disposed adjacent said ledge.

* * * * *